United States Patent [19]

Noguchi et al.

[11] Patent Number: 5,380,360
[45] Date of Patent: Jan. 10, 1995

[54] ULTRA-FINE GRANULAR BARIUM SULFATE-COATED FLAKY PIGMENT AND METHOD OF PREPARING THE SAME

[75] Inventors: Tamio Noguchi; Yumiko Waragai, both of Fukushima, Japan

[73] Assignee: Merck Patent Gesellschaft Mit Beschrankter Haftung, Darmstadt, Germany

[21] Appl. No.: 45,066

[22] Filed: Apr. 12, 1993

[30] Foreign Application Priority Data

Apr. 10, 1992 [JP] Japan .................. 4-134100

[51] Int. Cl.⁶ .............................. C04B 14/20
[52] U.S. Cl. .................... 106/415; 106/418; 106/436; 106/456; 428/363; 428/403
[58] Field of Search ............ 106/415, 418, 436, 456; 428/363, 403

[56] References Cited

U.S. PATENT DOCUMENTS

| 3,706,586 | 12/1972 | Meldrum et al. | 106/415 |
| 4,134,776 | 1/1979 | Rieger et al. | 106/417 |
| 4,272,397 | 6/1981 | Fukuda et al. | 106/415 |
| 4,435,220 | 3/1984 | Watanabe et al. | 106/415 |
| 4,509,988 | 4/1985 | Bernhard | 106/418 |
| 4,603,047 | 7/1986 | Watanabe et al. | 106/416 |
| 4,956,019 | 9/1990 | Noguchi et al. | 106/417 |
| 5,118,352 | 6/1992 | Noguchi | 106/415 |
| 5,288,481 | 2/1994 | Ounanian et al. | 424/63 |

Primary Examiner—Mark L. Bell
Assistant Examiner—Deborah Jones
Attorney, Agent, or Firm—Millen, White, Zelano & Branigan

[57] ABSTRACT

Disclosed are a flaky pigment in which the surfaces of fine flaky grains, as a pigment base, have been coated with ultra-fine barium sulfate grains having a mean grain size of 0.1 μm or less. The pigment is produced by a process comprising reacting:

(a) an aqueous solution containing a complexing agent capable of forming a complex compound with barium ion, as dissolved therein;

(b) an aqueous solution containing a water-soluble barium compound as dissolved therein; and (c) an aqueous solution containing sulfate ion. The invention involves this method of preparing the flaky pigment, and use of the pigment in pigment coloration of cosmetics, top coats for cars, plastics, printing inks, domestic electrical appliances, coating materials and coating paints for building materials.

16 Claims, No Drawings

ULTRA-FINE GRANULAR BARIUM SULFATE-COATED FLAKY PIGMENT AND METHOD OF PREPARING THE SAME

BACKGROUND OF THE INVENTION

The present inventors have previously provided a flaky pigment in which the surfaces of fine flaky grains, as a pigment base, have been coated with barium sulfate grains, as an extender pigment for face powder which has excellent adhesiveness to the skin and excellent masking power to give desired gloss and transparency when applied to the skin (Japanese Patent Publication Nos. 2-42387 and 2-42388, corresponding to U.S. Pat. No. 4,603,047).

In the above-mentioned flaky pigment, the grain size of the barium sulfate grains to be deposited on the surfaces of the base pigment grains is large, i.e., from 0.5 to 2.0 μm as a mean grain size. Therefore, the adhesiveness of the flaky pigment to the skin is not sufficient. It would be desirable for an extender pigment in face powder to have a wrinkle-masking effect due to scattering of light thereon, but the effect of the prior art flaky pigment is insufficient.

Japanese Patient Application Laid-Open No. 61-123673 has disclosed "pearl luster pigment and method of preparing the same" in which barium sulfate has been deposited on the surfaces of mica grains. However, the published specification of the patent application does not mention the method of preparing the pigment. In accordance with a method where barium sulfate and fine mica powder are merely blended so as to deposit barium sulfate on the surfaces of mica grains, fine grains of barium sulfate could not be uniformly deposited on the surfaces of mica grains.

In the case of a titanium oxide-coated mica which is generally used as a pearl luster pigment, the refractive index (n) of titanium oxide is 2.52 while that of mica is 1.56 so that the difference in the refractive index between them is large. As compared with mica as coated with titanium oxide (n=2.52) or iron oxide (n=3.0) having a large refractive index, mica as coated with barium sulfate has a small difference in the refractive index between barium sulfate (n=1.64) and mica (n=1.56). In addition, since the refractive indices of barium sulfate and mica are almost the same as those of coating paints or plastics (polyethylene, n=1.51 to 1.54; acrylic resins, n - 1.50 to 1.57), the pigment of barium sulfate/mica could not display the pearl luster pigment gloss and chroma when it is incorporated into coating paints or plastics.

SUMMARY OF THE INVENTION

An object of the present invention is to provide an ultra-fine granular barium sulfate-coated flaky pigment as prepared by depositing ultra-fine barium sulfate grains having a mean grain size of 0.1 μm or less on the surfaces of fine flaky pigment grains, the thus coated flaky pigment having improved adhesiveness to the skin and improved spreadability on the skin and also having a light-scattering effect to be attained by the ultra-fine barium sulfate grains.

In addition, the present invention also provides a method of preparing an ultra-fine granular barium sulfate-coated flaky pigment as mentioned below.

Upon further study of the specification and appended claims, further objects and advantages of this invention will become apparent to these skilled in the art.

DETAILED DESCRIPTION

The ultra-fine granular barium sulfate-coated flaky pigment is prepared by applying the following aqueous solutions (a), (b) and (c) to a suspension of a substrate which is fine flaky grains, as a pigment base, suspended in water; the method being characterized in that (a) is added to the suspension with stirring and then (b) and (c) are simultaneously added thereto, or an aqueous solution of (a) and (b) (prepared by adding (a) to (b)) and (c) are simultaneously added to the suspension with stirring, whereby the surfaces of the fine flaky pigment base grains are coated with ultra-fine barium sulfate grains having a mean grain size of 0.1 μm or less:

(a) an aqueous solution containing a complexing agent capable of forming a complex compound with barium ion, as dissolved therein;

(b) an aqueous solution containing a water-soluble barium compound dissolved therein; and (c) an aqueous solution containing sulfate ions.

Specifically, the present invention relates to an ultra-fine granular barium sulfate-coated flaky pigment and a method of preparing the same, in which a barium ion-containing aqueous solution and a sulfate ion-containing aqueous solution are simultaneously added to a suspension of fine flaky pigment grains, such as those of mica, talc, kaolin or sericite, with stirring in the presence of a complexing agent capable of forming a complex compound with barium ion whereby ultra-fine granular barium sulfate grains having a mean grain size of 0.1 μm or less are formed on the surfaces of the fine flaky pigment grains. Preferably, the grains have a mean size of 0.01–0.1 μm.

If desired, the ultra-fine granular barium sulfate-coated flaky mica pigment of the present invention can be further coated with fine grains of titanium oxide or iron oxide, which are generally used as a pigment for face powder, on the surfaces of the coated mica grains to give a higher functional pigment product.

As examples of metal oxides which are to be coated on the surfaces of the flaky pigment grains of the present invention for the purpose of imparting higher functional properties thereto as mentioned above, there are mentioned titanium oxide, aluminum oxide, iron oxide, zirconium oxide and zinc oxide; as examples of metal hydroxides which are also used for this purpose, there are mentioned iron hydroxide, titanium oxyhydroxide and aluminum hydroxide; and as examples of metal carbonates which are also used for this purpose, there are mentioned magnesium carbonate and calcium carbonate.

As the above-mentioned flaky pigment base in the present invention, usable is a flaky fine powder of mica, sericite, talc, kaolin or the like, preferably having a gain size of from 0.5 to 100 μm. As the suspension of such a flaky fine powder, preferred is one prepared by suspending from 5 to 20 parts of the fine powder in 100 parts of water. As the above-mentioned aqueous solution (a), usable is an aqueous solution as prepared by dissolving, preferably from 0.05 to 5 equivalents with respect to the barium ion in the aqueous solution (b), of a barium ion-complex compound-forming agent in water. The percentage of barium sulfate with respect to the mass of the pigment preferably is about 5–60%.

The temperature of the suspension is preferably from 50° to 95° C., more preferably from 60° to 80° C.

As examples of the complexing agent for use in the present invention, there are mentioned citric acid, tartaric acid, Tiron (catechol-3,5-disulfonic acid), ethylenediaminetetraacetate (EDTA), phthalic acid, glutamic acid, 1,2-diaminocyclohexanetetraacetic acid (DCTA), diethylenetriaminepentaacetic acid (DTPA), ethylene glycol-bis(2-aminomethyl ether)-tetraacetic acid (EGTA), 2-hydroxyethylethylenediamine-triacetic acid (HEDTA), nitrilotriacetic acid (NTA), etc.; however, it is contemplated that any agent capable of forming a complex with barium ions under reaction conditions is included in the invention.

The complexing agent may directly be added to the aqueous solution (b).

As examples of the barium compound for use in the present invention, there are mentioned barium chloride, barium hydroxide, barium nitrate, barium carbonate, etc.

In preparing the above-mentioned aqueous solution (c), sulfuric acid, sodium sulfate, potassium sulfate, magnesium sulfate, ammonium sulfate or the like is used.

Where the pigment of the present invention is applied to particular uses, for example, to cosmetics, addition of an aqueous diluted sulfuric acid solution to the pigment, after formation of barium sulfate therein, is preferred so as to eliminate residual barium ions in the pigment. For instance, a diluted sulfuric acid of from 5 to 30% by weight is used to give a solution having pH of from 1 to 2. After addition of such an aqueous diluted sulfuric acid to the pigment, an aqueous solution of sodium hydroxide of from 5 to 30% by weight is added thereto so as to bring the pH to a value within the range of from 4 to 7. The thus obtained solid product is removed by filtration, washed and then dried at 105° C. for 12 hours.

Thus, an ultra-fine granular barium sulfate-coated flaky pigment is obtained.

In depositing the ultra-fine granular barium sulfate on the surfaces of the fine flaky pigment base grains, use of the above-mentioned barium ion-complexing agent is important so as to control and retard the rapid crystal growth of barium sulfate crystals to thereby form the intended fine grains of barium sulfate. Table 1 below shows the stability constant (log Kstab) of barium complexes each with the above-mentioned complexing agent as coordinated to barium.

TABLE 1

| Complexing Agent | Metal Ion | Complex | Components | log Kstab |
|---|---|---|---|---|
| Phthalic Acid<br>$C_6H_4(COOH)_2 = H_2L$ | $Ba^{2+}$ | BaL | Ba + L | 1.5 |
| Acetic Acid<br>$CH_3COOH = HL$ | $Ba^{2+}$ | BaL | Ba + L | 0.4 |
| Citric Acid<br>$C_3H_4(OH)(COOH)_3 = H_4L$ | $Ba^{2+}$ | BaHL | Ba + HL | 2.56 |
| Tartaric Acid<br>$H_3C_4H_4O_6 = H_2L$ | $Ba^{2+}$ | BaHL | Ba + HL | 2.54 |
| Nitrilotriacetic Acid<br>NTA = $H_3L$ | $Ba^{2+}$ | BaHL | Ba + HL | 4.82 |
| Diethylenetriaminepentaacetic Acid<br>DTPA = $H_4L$ | $Ba^{2+}$ | BaHL | Ba + HL | 8.63 |
| Ethylenediaminetetraacetate<br>EDTA = $H_4L$ | $Ba^{2+}$ | BaHL | Ba + HL | 7.76 |

As the complexing agent for forming the desired ultra-fine granular barium sulfate, citric acid and tartaric acid having a large stability constant value are preferred to phthalic acid and acetic acid having a small stability constant value (refer to Table 2 below).

Where coating of pigment grains with barium sulfate is effected in the absence of the above-mentioned complexing agent, ultra-fine barium sulfate grains having a mean grain size of 0.1 μm or less could not be deposited on the surfaces of fine flaky pigment grains but random deposition of barium sulfate grains having a large grain size on the surfaces of pigment grains occurs.

Table 2 below shows examples of the grain size of barium sulfate grains to be formed on the surfaces of muscovite grains, to which the above-mentioned method of the present invention has been applied.

TABLE 2

| $Ba^{2+}$ | $SO_4^{2-}$ | Complexing Agent | Stability Constant | Grain Size of $BaSO_4$(μm) |
|---|---|---|---|---|
| $Ba(OH)_2$ | $H_2SO_4$ | — | — | 0.20 to 0.40 |
| $Ba(OH)_2$ | $H_2SO_4$ | tartaric acid | 2.54 | 0.08 to 0.13 |
| $Ba(OH)_2$ | $H_2SO_4$ | citric acid | 2.56 | 0.03 to 0.07 |
| $Ba(OH)_2$ | $H_2SO_4$ | trisodium citrate | 2.56 | 0.04 to 0.08 |
| $Ba(OH)_2$ | $H_2SO_4$ | tripotassium citrate | 2.56 | 0.04 to 0.08 |
| $Ba(OH)_2$ | $H_2SO_4$ | tricalcium citrate | 2.56 | 0.03 to 0.27 |
| $Ba(OH)_2$ | $H_2SO_4$ | trimagnesium citrate | 2.56 | 0.04 to 0.10 |
| $Ba(OH)_2$ | $H_2SO_4$ | NTA | 4.82 | 0.05 to 0.13 |
| $Ba(OH)_2$ | $H_2SO_4$ | EDTA | 7.76 | 0.03 to 0.02 |
| $Ba(OH)_2$ | $H_2SO_4$ | DTPA | 8.63 | 0.03 to 0.04 |

Table 3 below shows physical values of flaky mica pigments each as coated with fine barium sulfate grains having a different grain size.

As is noted from the data in Table 3, the flaky pigment sample of the present invention has a small angle of repose and therefore has improved spreadability on the skin. In addition, it has a large oil absorption. From the values, it is understood that the sample of the present invention is a powder which can absorb well the secreted sebum and which can adhere well to the skin.

TABLE 3

| No. | Grain Size (μm) | Amount of Barium Sulfate Coated (wt. %) | Grain Size of Barium Sulfate (μm) | Specific Surface Area (m$^2$/g) | Angle of Repose | Oil Absorption (ml/100 g) |
| --- | --- | --- | --- | --- | --- | --- |
| 0 | 1 to 15 | — | — | 7.0 | 52 | 52.5 |
| 1 | 1 to 15 | 20 | 0.2 to 1.4 | 6.1 | 52 | 72.0 |
| 2 | 1 to 15 | 20 | 0.2 to 0.4 | 8.6 | 48 | 71.2 |
| 3 | 1 to 15 | 20 | 0.04 to 0.08 | 9.9 | 47 | 79.3 |

Notes:
No. 0: Mica only.
Nos. 1 and 2: Comparative samples by prior art.
No. 3: Sample of the invention.
Angle of Repose is the direct indication of the potential flowabilities of material and is measured from the heap carefully built up by dropping the material from vibrating screen and glass funnel above the horizontal plate.

One embodiment of producing the above-mentioned flaky pigment in accordance with the method of the present invention will be mentioned below concretely.

15 Parts of muscovite powder is suspended in 100 parts of water, and a barium ion-complexing agent (e.g., trisodium citrate) is added thereto in an amount of from 0.02 to 0.20 equivalent to barium compound. This is heated at a temperature of from 50° to 90° C., preferably from 60° to 80° C., and an aqueous solution containing from 5 to 30% by weight of sulfuric acid and an aqueous solution containing from 5 to 25% by weight of a barium compound are simultaneously added thereto with stirring. After addition, the pH value of the resulting suspension is adjusted to be 2 by adding an aqueous sulfuric acid solution thereto. Then, an aqueous solution of from 5 to 30% by weight of a titanium metal salt and an aqueous solution of from 5 to 30% by weight of sodium hydroxide are simultaneously added thereto. After addition, the pH value of the resulting suspension is adjusted to be from 5 to 7 by adding an aqueous sodium hydroxide solution thereto. Then, the solid product formed is taken out by filtration, washed and dried at 105° C. for 12 hours, and thereafter fired at 500° to 800° C. for 0.5 to 2 hours. As a result, a muscovite pigment coated with both ultra-fine granular barium sulfate and titanium oxide is obtained.

The thus prepared flaky pigment was identified to have fine barium sulfate grains and titanium oxide grains as deposited on the surfaces of the fine flaky pigment base grains, by observation thereof with an electromicroscope and a mineral microscope and from the results of analysis thereof by X-ray diffraction. The characteristics of the flaky pigment samples thus prepared are shown in Table 4 below. As is noted from the powder characteristic values in Table 4, the pigment samples have good adhesiveness to the skin and good spreadability on the skin and also have smooth and soft feeling and a satisfactory color tone.

TABLE 4

| No. | Grain Size (μm) | Amount of Barium Sulfate Coated (wt. %) | Amount of Titanium Oxide Coated (wt. %) | Specific Surface Area (m$^2$/g) | Angle of Repose | Oil Absorption (ml/100 g) |
| --- | --- | --- | --- | --- | --- | --- |
| 1 | 1 to 15 | 25 (grain size of barium sulfate grains, 0.2 to 0.4 μm) | 15 | 16.1 | 53 | 121.5 |
| 2 | 1 to 15 | 22 (grain size of barium sulfate grains, 0.02 to 0.10 μm) | 11 | 13.6 | 53 | 137.0 |

Recently, pigments of the kind having a delustering effect are apt to be used not only in cosmetics but also in printing inks, coating paints and plastics. Therefore, the pigment to be obtained by the present invention is useful also as a delustering pigment, i.e. one which decreases or removes luster of compositions to which it is added.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are be weight.

The entire disclosure of all applications, patents and publications, cited above and below, and of corresponding Japanese application No. JP 92-134100, filed Apr. 10, 1992, are hereby incorporated by reference.

EXAMPLES

Example 1

150 g of a fine powder of muscovite having a diameter of from 1 to 15 μ was suspended in 1,600 ml of water and heated up to 60° C., and an aqueous solution of 2.5 g of sodium citrate as dissolved in 25 ml of water was added thereto with stirring.

To the resulting suspension were dropwise added simultaneously an aqueous solution of 23 g of sodium sulfate and 2.5 g of sulfuric acid as dissolved in 129 g of water and an aqueous solution of 51.1 g of barium hydroxide dissolved in 289 g of water, at a flow rate of 28 ml/min and 64 ml/min, respectively. After the addition, the whole was stirred for 30 minutes, and an aqueous solution of 30% by weight of sulfuric acid was added thereto to make pH of 1. This was stirred for one further hour, and an aqueous solution of 32% by weight of sodium hydroxide was added thereto at a flow rate of 4 ml/min, to make pH of 5.

The solid product thus formed was precipitated and was taken out by filtration. This was washed with water to remove salts therefrom and then dried at about 105 to 110° C. for 8 hours.

As a result, a pigment coated with barium sulfate having a mean grain size of 0.1 μm was obtained, which had good spreadabililty and adhesiveness.

Example 2

189 g of a fine powder of sericite having a grain size of from 1 to 20 μm was suspended in one liter of water and heated up to 60° C., and 6 g of trisodium citrate dihydrate was added thereto with stirring. To the resulting suspension were dropwise added simultaneously an aqueous solution of 28.8 g of anhydrous sodium sulfate and 3.2 g of concentrated sulfuric acid as dissolved in 163 g of water and an aqueous solution of 64 g of barium hydroxide dihydrate dissolved in 362 g of water, at a flow rate of 35 ml/min and 80 ml/min, respectively. After the addition, the whole was stirred for 30 minutes, and an aqueous solution of 30% by weight of sulfuric acid was added thereto to make pH of 1. This was stirred for one further hour, and an aqueous solution of 32% by weight of sodium hydroxide was added thereto to make a pH of 5.

The solid product thus formed was precipitated and was taken out by filtration. This was washed with water to remove salts therefrom and then dried at about 105 to 110° C. for 8 hours.

As a result, a pigment coated with barium sulfate having a mean grain size of 0.1 μm was obtained, which had good spreadabililty and adhesiveness.

Example 3

189 g of a fine powder of talc having a grain size of from 3 to 24 μm was suspended in one liter of water and heated up to 60° C., and 6 g of trisodium citrate dihydrate was added thereto with stirring. To the resulting suspension were dropwise added simultaneously an aqueous solution oil 28.8 g of anhydrous sodium sulfate and 3.2 g of concentrated sulfuric acid dissolved in 163 g of water and an aqueous solution of 64 g of barium hydroxide dihydrate dissolved in 362 g of water, at a flow rate of 35 ml/min and 80 ml/min, respectively. After the addition, the whole was stirred for 30 minutes, and an aqueous solution of 30% by weight of sulfuric acid was added thereto to make pH of 1. This was stirred for one further hour, and an aqueous solution of 32% by weight of sodium hydroxide was added thereto to make a pH of 5.

The solid product thus formed was precipitated and was taken out by filtration. This was washed with water to remove salts therefrom and then dried at about 105 to 110° C. for 8 hours.

As a result, a pigment as coated with barium sulfate having a mean grain size of 0.1 μm was obtained, which had good spreadability and adhesiveness.

Example 4

189 g of a fine powder of kaolin having a grain size of from 0.5 to 15 μm was suspended in one liter of water and heated up to 60° C., and 6 g of trisodium citrate dihydrate was added thereto with stirring. To the resulting suspension were dropwise added simultaneously an aqueous solution 28.8 g of anhydrous sodium sulfate and 3.2 g of concentrated sulfuric acid dissolved in 163 g of water and an aqueous solution of 64 g of barium hydroxide dihydrate dissolved in 362 g of water, at a flow rate of 35 ml/min and 80 ml/min, respectively. After the addition, the whole was stirred for 30 minutes, and an aqueous solution of 30% by weight of sulfuric acid was added thereto to make a pH of 1. This was stirred for one further hour, and an aqueous solution of 32% by weight of sodium hydroxide was added thereto to make a pH of 5.

The solid product thus formed was precipitated and was taken out by filtration. This was washed with water to remove salts therefrom and then dried at about 105 to 110° C. for 8 hours.

As a result, a pigment coated with barium sulfate having a mean grain size of 0.1 μm was obtained, which had good spreadability and adhesiveness.

Example 5

150 g of a fine powder of muscovite having a diameter of from 1 to 15 μm was suspended in 1,600 ml of water and heated up to 60° C., and an aqueous solution of 3.5 g of citric acid as dissolved in 25 ml of water was added thereto with stirring.

To the resulting suspension were dropwise added simultaneously an aqueous solution of 23 g of sodium sulfate and 2.5 g of sulfuric acid dissolved in 129 g of water and an aqueous solution of 51.1 g of barium hydroxide dissolved in 289 g of water, at a flow rate of 28 ml/min and 64 ml/min, respectively. After the addition, the whole was stirred for 30 minutes, and an aqueous solution of 30% by weight of sulfuric acid was added thereto to make a pH of 1. This was stirred for one further hour, and an aqueous solution of 32% by weight of sodium hydroxide was added thereto at a flow rate of 4 ml/min, to make a pH of 5.

The solid product thus formed was precipitated and was taken out by filtration. This was washed with a water to remove salts therefrom and then dried at about 105 to 110° C. for 8 hours.

As a result, a pigment comprising muscovite grains coated with barium sulfate having a mean grain size of 0.1 μm was obtained, which had good spreadability and adhesiveness.

Example 6

150 g of a fine powder of muscovite having a diameter of from 1 to 15 μm was suspended in 1,600 ml of water and heated up to 60° C., and an aqueous solution of 3.9 g of nitrilotriacetic acid dissolved in 25 ml of water was added thereto with stirring.

To the resulting suspension were dropwise added simultaneously an aqueous solution of 23 g of sodium sulfate and 2.5 g of sulfuric acid dissolved in 129 g of water and an aqueous solution of 51.1 g of barium hydroxide dissolved in 289 g of water, at a flow rate of 28 ml/min and 64 ml/min, respectively. After the addition, the whole was stirred for 30 minutes, and an aqueous solution of 30% by weight of sulfuric acid was added thereto to make a pH of 1. This was stirred for one further hour, and an aqueous solution of 32% by weight of sodium hydroxide was added thereto at a flow rate of 4 ml/min, to make a pH of 5.

The solid product thus formed was precipitated and was taken out by filtration. This was washed with water to remove salts therefrom and then dried at about 105 to 110° C. for 8 hours.

As a result, a pigment comprising muscovite grains coated with barium sulfate having a mean grain size of 0.1 μm was obtained, which had good spreadability and adhesiveness.

Example 7

150 g of a fine powder of muscovite having a diameter of from 1 to 15 μm was suspended in 1,600 ml of water and heated up to 60° C., and an aqueous solution of 7.6 g of ethylenediaminetetraacetate as dissolved in 25 ml of water was added thereto with stirring.

To the resulting suspension were dropwise added simultaneously an aqueous solution of 23 g of sodium sulfate and 2.5 g of sulfuric acid dissolved in 129 g of water and an aqueous solution of 51.1 g of barium hydroxide dissolved in 289 g of water, at a flow rate of 28 ml/min and 64 ml/min, respectively. After the addition, the whole was stirred for 30 minutes, and an aqueous solution of 30% by weight of sulfuric acid was added thereto to make a pH of 1. This was stirred for one further hour, and an aqueous solution of 32% by weight of sodium hydroxide was added thereto at a flow rate of 4 ml/min, to make a pH of 5.

The solid product thus formed was precipitated and was taken out by filtration. This was washed with water to remove salts therefrom and then dried at about 105 to 110° C. for 8 hours.

As a result, a pigment comprising muscovite grains coated with barium sulfate having a mean grain size of 0.1 μm was obtained, which had good spreadability and adhesiveness.

Example 8

150 g of a fine powder of muscovite having a diameter of from 1 to 15 μm was suspended in 1,600 ml of water and heated up to 60° C., and an aqueous solution of 3.1 g of tartaric acid as dissolved in 25 ml of water was added thereto with stirring.

To the resulting suspension were dropwise added simultaneously an aqueous solution of 23 g of sodium sulfate and 2.5 got sulfuric acid dissolved in 129 g of water and an aqueous solution of 51.1 g of barium hydroxide dissolved fin 289 g of water, at a flow rate of 28 ml/min and 64 ml/min, respectively. After the addition, the whole was stirred for 30 minutes, and an aqueous solution of 30% by weight of sulfuric acid was added thereto to make a pH of 1. This was stirred for one further hour, and an aqueous solution of 32% by weight of sodium hydroxide was added thereto at a flow rate of 4 ml/min, to make a pH of 5.

The solid product thus formed was precipitated and was taken out by filtration. This was washed with water to remove salts therefrom and then dried at about 105 to 10° C. for 8 hours.

As a result, a pigment comprising muscovite grains coated with barium sulfate having a mean grain size of 0.1 μm was obtained, which had good spreadability and adhesiveness.

Example 9

150 g of a fine powder of muscovite having a diameter of from 1 to 15 μm was suspended in 1,600 ml of water and heated up to 60° C., and an aqueous solution of 8 g of diethylenetriamine-pentaacetic acid as dissolved in 25 ml of water was added thereto with stirring.

To the resulting suspension were dropwise added simultaneously an aqueous solution of 23 g of sodium sulfate and 2.5 g of sulfuric acid dissolved in 129 g of water and an aqueous solution of 51.1 g of barium hydroxide dissolved in 289 g of water, at a flow rate of 28 ml/min and 64 ml/min, respectively. After the addition, the whole was stirred for 30 minutes, and an aqueous solution of 30% by weight of sulfuric acid was added thereto to make a pH of 1. This was stirred for one further hour, and an aqueous solution of 32% by weight of sodium hydroxide was added thereto at a flow rate of 4 ml/min, to make a pH of 5.

The solid product thus formed was precipitated and was taken out by filtration. This was washed with water to remove salts therefrom and then dried at about 105° to 110° C. for 8 hours.

As a result, a pigment comprising muscovite grains coated with barium sulfate having a mean grain size of 0.1 μm was obtained, which had good spreadability and adhesiveness.

Example 10

151 g of a fine powder of muscovite having a diameter of from 1 to 15 μm was suspended in 2.2 liters of water and heated up to 60° C., and 3.3 g of trisodium citrate dihydrate was added thereto with stirring. To the resulting suspension were dropwise added simultaneously an aqueous solution of 30.7 g of anhydrous sodium sulfate and 3.3 g of concentrated sulfuric acid dissolved in 173 g of water and an aqueous solution of 68.2 g of barium hydroxide dihydrate dissolved in 386 g of water, at a flow rate of 28 ml/min and 64 ml/min, respectively. After the addition, the whole was stirred for 30 minutes, and an aqueous solution of 30% by weight of sulfuric acid was added thereto to make a pH of 2. This was stirred for one further hour and then heated up to 75° C., and 152 ml of an aqueous solution of 394 g/liter of titanium tetrachloride and an aqueous solution of by weight of sodium hydroxide were dropwise added thereto simultaneously. After the addition, the solution was made to have a pH of 5 with an aqueous solution of 32% by weight of sodium hydroxide.

The solid product thus formed was precipitated and was taken out by filtration. This was washed with water to remove salts therefrom and then dried at about 105 to 110° C. for 8 hours.

As a result, a body pigment having good spreadability and adhesiveness was obtained.

Example 11

151 g of a fine powder of muscovite having a diameter of from 1 to 15 μm was suspended in 2.2 liters of water and heated up to 60° C., and 3.3 g of trisodium citrate dihydrate was added thereto with stirring. To the resulting suspension were dropwise added simultaneously an aqueous solution of 30.7 g of anhydrous sodium sulfate and 3.3 g of concentrated sulfuric acid dissolved in 173 g of water and an aqueous solution of 68.2 g of barium hydroxide dihydrate dissolved in 386 g of water, at a flow rate of 28 ml/min and 64 ml/min, respectively. After the addition, the whole was stirred for 30 minutes, and an aqueous solution of 30% by weight of sulfuric acid was added thereto to make a pH of 2. This was stirred for one further hour and then heated up to 70° C., and 259 g of an aqueous solution of 19.5% by weight of titanyl sulfate was dropwise added thereto at a flow rate of 2 ml/min. After the addition, this was stirred for 30 minutes and then an aqueous solution of 32% by weight of potassium hydroxide was added thereto to make a pH of 5.

The solid product thus formed was precipitated and was taken out by filtration. This was washed with water to remove salts therefrom, then dried at about 105 to 110° C. for 8 hours and fired at 750° C. for 40 minutes.

As a result, an extender pigment having good spreadability and adhesiveness was obtained.

Use Example

A compact powder comprising the following components was prepared.

| Extender Pigment Prepared in Example 10 | 50 g |
|---|---|
| Colored Pigment | 5 g |
| Lanolin | 3 g |
| Isopropyl Myristate | 3 g |
| Magnesium Stearate | 2 g |
| Corn Starch | 12 g |
| Talc | 25 g |

The compact powder thus prepared was extremely excellent and satisfactory in the spreadability, adhesiveness, smoothness, soft feeling and color tone.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A flaky pigment comprising a flaky substrate uniformly coated with ultra-fine barium sulfate grains having a maximum mean grain size of 0.1 μm.

2. A pigment according to claim 1, wherein the substrate is mica, talc, kaolin or sericite.

3. A pigment according to claim 2, wherein the substrate has a grain size of 0.5–100 μm.

4. A pigment according to claim 1, wherein the mean grain size of the barium sulfate is 0.04 to 0.08 μm.

5. A pigment according to claim 1, comprising a further layer of titanium oxide or iron oxide.

6. A pigment according to claim 1, comprising a further layer of an oxide of aluminum, zirconium or zinc, a hydroxide of iron, titanium, or aluminum, or a carbonate of magnesium or calcium.

7. A method for the preparation of an ultra-fine granular barium sulfate-coated flaky pigment, comprising:
   (a) adding to a suspension of a flaky substrate an aqueous solution containing a complexing agent capable of forming a complex with barium ions, and then simultaneously adding an aqueous solution containing a water-soluble barium compound dissolved therein, and an aqueous solution of sulfate ions; or
   (b) combining said complexing agent and aqueous solution of water-soluble barium compound, and adding resultant combination to a suspension of flaky substrate simultaneously with an aqueous solution of sulfate ion.

8. A method for the preparation of an ultra-fine granular barium sulfate-coated flaky pigment, comprising:
   (a) adding simultaneously an aqueous solution of a water-soluble barium compound and an aqueous solution of sulfate ions, to a suspension of a flaky substrate and an aqueous solution of a complexing agent capable of forming a complex with barium ions; or
   (b) adding simultaneously to a suspension of a flaky substrate (i) a mixture of a solution containing a complexing agent capable of forming a complex with barium ions with an aqueous solution of a water-soluble barium compound and (ii) an aqueous solution of sulfate ions.

9. A method according to claim 7, wherein the complexing agent is citric acid, tartaric acid, catechol-3,5-disulfonic acid, EDTA, phthalic acid, glutamic acid, DCTA, DTPA, EGTA, HEDTA or NTA.

10. A method according to claim 7, wherein the barium compound is barium chloride, barium hydroxide, barium nitrate or barium carbonate.

11. A method according to claim 7, wherein the solution of sulfate ions is a solution of sulfuric acid, sodium sulfate, potassium sulfate, magnesium sulfate or ammonium sulfate.

12. A method according to claim 7, wherein subsequent to the formation of barium sulfate on the substrate, aqueous dilute sulfuric acid is added so as to neutralize residual barium ions in the pigment.

13. A method according to claim 12, wherein subsequent to the neutralization of the residual ions the pH of the solution is adjusted to 4–7.

14. A pigment produced by the process of claim 7.

15. A pigment produced by the process of claim 8.

16. A pigment produced by the process of claim 9.

* * * * *